United States Patent [19]

Mammolenti et al.

[11] Patent Number: 4,601,697
[45] Date of Patent: Jul. 22, 1986

[54] LONG INDWELLING DOUBLE BORE CATHETER

[75] Inventors: Joseph Mammolenti, Granger; Bruce J. Oberhardt, Mishawaka, both of Ind.

[73] Assignee: Miles Laboratories, Inc., Elkhart, Ind.

[21] Appl. No.: 679,447

[22] Filed: Dec. 7, 1984

Related U.S. Application Data

[63] Continuation of Ser. No. 437,880, Oct. 29, 1982, abandoned.

[51] Int. Cl.$^4$ .............................................. A61M 3/00
[52] U.S. Cl. ...................................... 604/43; 604/269
[58] Field of Search ................... 604/4, 27, 43–46, 604/82–83, 264, 272, 280, 53, 269

[56] References Cited

U.S. PATENT DOCUMENTS

| | | | |
|---|---|---|---|
| 2,286,462 | 6/1942 | Chaffin | 604/43 |
| 3,512,517 | 5/1970 | Kadish et al. | 604/27 |
| 3,610,226 | 10/1971 | Albisser | 604/27 |
| 3,916,892 | 11/1975 | Latham, Jr. | 604/83 |
| 4,069,814 | 1/1978 | Clemens | 604/27 |
| 4,280,496 | 7/1981 | Van Baelen | 604/83 |
| 4,318,402 | 3/1982 | Vaillancourt | 604/56 |
| 4,405,313 | 9/1983 | Sisley et al. | 604/43 |

OTHER PUBLICATIONS

Gander et al., "An All-Plastic Double-Lumen Catheter for Continuous Blood Sampling", *Medical Instrumentation*, vol. 9, No. 4, Jul.–Aug. 1975.

*Primary Examiner*—C. Fred Rosenbaum
*Assistant Examiner*—Michelle Lester
*Attorney, Agent, or Firm*—Roger N. Coe

[57] ABSTRACT

A long indwelling double bore catheter for dilution and sampling of blood on a continuing basis capable of being used for long periods of time. The long indwelling double bore catheter has a small mixing chamber with an opening of a cross-sectional area equal to or less than the combined cross-sectional areas of the double bores, said opening communicating with the body fluid, e.g., blood, to be sampled, and wherein the distance of the mixing chamber from the distal end of the double bores to the end of the catheter is equal to or greater than 2 millimeters. Preferably, the volume of the mixing chamber is between about 3 and about $9 \times 10^{-5}$ cubic inches. Preferably, the opening which communicates with the body fluid is a noncircular elongated opening which is equal to or less than twice the combined cross-sectional areas of the double bores.

1 Claim, 6 Drawing Figures

LONG INDWELLING DOUBLE BORE CATHETER

This is a continuation, of application Ser. No. 437,880, filed Oct. 29, 1982, now abandoned.

BACKGROUND OF THE INVENTION

1. Field of the Invention

The present invention relates to catheter devices for continuous analysis of body fluids and, in particular, relates to a long indwelling double bore catheter which may be inserted into a fluid carrying member of a living being for long periods of time to provide a continuous fluid flow for analysis.

2. Description of the Prior Art

In hospital and clinical establishments, as well as in research facilities, it is frequently necessary to slowly withdraw blood samples from a human patient or an experimental animal over an extended period of time, analyze the blood and, in some cases, return the blood to the patient or animal. This is conveniently accomplished by inserting a flexible tube cannula into a blood vessel, such as a vein or an artery, of the patient or animal and withdrawing blood as desired from the cannula. In order to prevent blood coagulation in the cannula or in associated tubing for conducting the blood sample from the cannula, it is usual practice to mix an anticoagulant material, such as heparin, with blood sample as soon as possible after it is withdrawn from the blood vessel. For this purpose, a double lumen cannula apparatus has been used for many years. In this double lumen apparatus a small diameter tube is inserted within the usual cannula sheath. The passage through this small diameter tube forms one lumen, and the annular space around the outer wall surface of the inner tube and the inner wall surface of the cannula sheath forms the other lumen. The inner tube terminates within the cannula sheath a short distance from the tip of the cannula sheath. In use, the anticoagulant material passes through the annular lumen toward the tip of the cannula sheath where it contacts and mixes with the blood entering the cannula from the blood vessel. The mixture of blood and anticoagulant material then flows out of the cannula through the inner tubular lumen of the double lumen cannula apparatus.

The prior art double lumen cannula apparatus typically has two principal problems. First, the distance between the end of the inner tubular lumen and the tip of the cannular sheath is not controlled with any high degree of precision. Most double lumen cannula apparatuses have a support body through which the inner tubular lumen and a conduit for anticoagulant material are passed. The cannula sheath, which normally has a funnel portion at one end and a tubular portion at the other end, is mated in conical press fit against the body so that the inner tubular lumen is coaxially within the tubular portion of the cannula sheath. Any variations in the length of the cannula sheath and/or of the inner tubular lumen or of the coaxial press fit between the cannular sheath and body can cause a variation in the distance between the end of the inner lumen and the tip of the cannula sheath. If this distance is undersirably short, some of the anticoagulant material from the annular lumen undesirably enters the blood vessel of the patient or animal. There could also be inadequate dilution of the blood sample by the anticoagulant material. This would cause false readings when the diluted blood sample is analyzed. If the distance is undesirably long, some of the blood may start to coagulate in the cannula sheath before it contacts the anticoagulant material.

When the cannula sheath mates against a support body, any variation in the final position of the mated parts from the desired position can cause an undesirable distance variation. Since the cannula sheath generally mates in a conical press fit over an extension of the main support body in most prior art apparatus, there is often considerable variation in the final position. This is caused both by tolerance in the tapers of the sheath and body and also by variations in the manual pressure employed to mate the sheath against the body. Prior art apparatus often employs a resilient material for the support body and its extension. The resiliency of this structural element can also cause undesirable dimensional variations in the assembled apparatus.

A second disadvantage of prior art apparatus is in the excessive volume of the introduction chamber for the anticoagulant material. In typical double lumen cannula apparatus the space in the funnel portion of the cannula sheath between the support body and the junction between the funnel and the tubular portion of the cannula sheath forms an introduction chamber for such material. In normal use, the cannula sheath is first inserted into the blood vessel. Blood begins to flow through the tubular portion and into the funnnel section of the cannular sheath. The catheter portion consisting of a support body, a first conduit forming an inner tubular lumen and a second conduit to provide the anticoagulant material is then inserted into the cannula sheath with the cannula sheath mating against the support body. The volume of blood initially in the cannula sheath and especially in the funnel portion occupies a space intended for introduction of the anticoagulant material and should be minimized to prevent slow response to changes in concentration of an analyte in the blood, as would occur with a large mixing chamber or other on line "dead volume" space. In addition, this volume has considerable variation in prior art apparatus. Moreover, movement of an inner lumen relative to an outer lumen can change flow rates in many prior art devices.

With the development of the double lumen cannula apparatus for blood sampling as set forth in U.S. Pat. No. 4,069,814, improved control over the dilution of a blood sample with anticoagulant material was achieved. Nevertheless, this catheter cannot be used effectively in situations requiring access to large, deep vessels, particularly in cases where small surface veins only are available. In these cases, it is necessary to use a longer catheter such that a deep vein can be accessed. Moreover, in some situations it is necessary to leave the catheter in for a long period of time and in those situations it is also advantageous to use a larger, deeper vein.

If one utilizes double bore tubing to achieve a long indwelling catheter, the diluent being pumped through one bore and the blood being pumped through the other bore, it is found that the diluent spills into the blood stream and reliably diluted blood samples cannot be obtained. If one restricts the opening beyond the tip the situation is improved, but the resulting device is still unsuitable for reliable use. Pulsations caused by the pumping means used will still cause periodic loss of diluent through the end opening.

There is also a need for a double lumen catheter which can be used as effectively in an upright position as in an inverted position, i.e., a catheter which is not position sensitive and, therefore, which does not change its flow rate with each change in the position of the patient.

SUMMARY OF THE INVENTION

In accordance with the present invention, a long indwelling double bore catheter for dilution and sampling of blood from a human patient or an experimental animal on a continuing basis for long periods of time is achieved. The long indwelling double bore catheter can be inserted in either an upright or inverted position without restriction of flow or spilling anticoagulant material into the blood stream.

Proper mixing of the anticoagulant material and the blood samples is achieved by a small mixing chamber located at the distal end of the double bores of the catheter, wherein the mixing chamber has an opening of a cross-sectional area equal to or less than the combined cross sectional areas of the double bores, said opening communicating with the body fluid, e.g., blood, to be sampled, and wherein the distance of the mixing chamber from the distal end of the double bores to the end of the catheter is equal to or greater than 2 millimeters (0.007 inches). Preferably, the volume of the mixing chamber is between about 3 and about $9 \times 10^{-5}$ cubic inches. Preferably, the opening which communicates with the body fluid is a noncircular elongated opening which is equal to or less than twice the combined cross sectional areas of the double bores.

BRIEF DESCRIPTION OF THE DRAWINGS

Other and further objects, advantages and features of the invention will be apparent to those skilled in the art from the following detailed description thereof, taken in conjunction with the accompanying drawings, in which.

DESCRIPTION OF THE INVENTION

Figure 1:
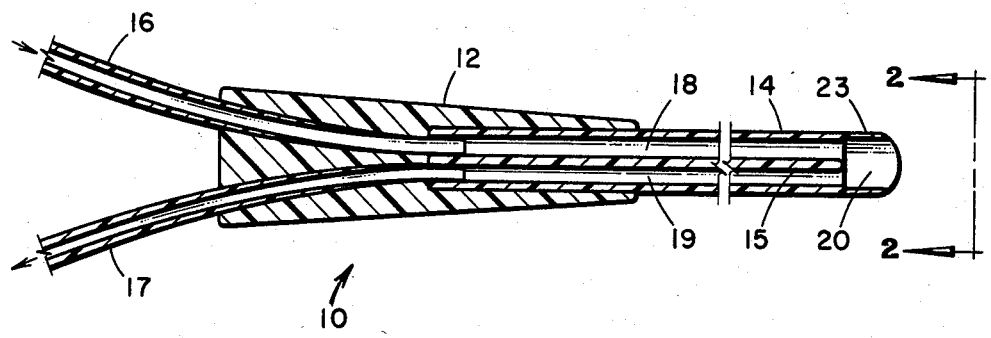
FIG. 1 is a partial cross-sectional view of one illustrative embodiment of a long indwelling double bore catheter of the present invention.

Referring to the drawings, the long indwelling double bore catheter 10 has a casing 12 surrounding double bore tubing 14 and 15 and flexible tubing 16 and 17 which interconnects with bores 18 and 19, respectively. Bores 18 and 19 terminate at the distal end in a mixing chamber 20 opposite the side of the mixing chamber which communicates with fluid, e.g., blood, to be sampled. The opening 22 (FIG. 2) of mixing chamber 20 which communicates with blood to be sampled is a noncircular elongated opening having a cross-sectional area equal to or less than two times ($2\times$) the combined cross-sectional areas of bores 18 and 19. The outer wall 23 of mixing chamber 20 also forms the outer wall of bores 18 and 19.

The preferred configuration of opening 22 is rectangular with rounded corners (or flattened ellipsoidal) and departs significantly from a circular opening of diameter sufficient to encompass the double bores. While any noncircular elongated opening is suitable, such that the appropriate configuration of the mixing chamber is maintained, the major axis of the noncircular opening should be approximately twice the minor axis.

The configuration of the present invention permits the double bore catheter and mixing chamber to be manufactured as one piece from double bore flexible tubing. The fact that the double bore catheter can be formed as one piece represents a significant advantage over prior art catheters which require that the tip be fabricated from a separate piece and attached to double bore tubing which then in turn is attached to flexible tubing. Not only does the latter design complicate manufacturing procedures, but, more importantly, there is always the associated potential problem that the tip of the catheter could eventually come off during use.

The diameter of bores 18 and 19 can be the same or different ranging from about 0.012 inch to 0.016 inch. The depth of the mixing chamber 20 is typically between 2 and 3 mm and the width of opening 22, and hence mixing chamber 20, is typically 0.02 inch. The height of opening 22 and mixing chamber 20 is typically about 0.04 inch.

Figure 1A:
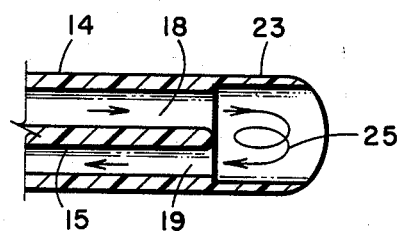
FIG. 1a is an enlarged view, in cross-section, of the distal end of the catheter of FIG. 1.
Figure 2:
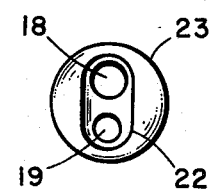
FIG. 2 represents an end view of the long indwelling double bore catheter of FIG. 1, taken along lines 2—2.

Thus, mixing chamber 20 takes on the configuration of opening 22 in FIGS. 1, 1a, and 2. The distance of the mixing chamber from the distal end of the double bores to the end of the catheter is equal to or greater than 2 millimeters (mm). The volume of the mixing chamber is kept small by this configuration to a volume between about 3 and about $9 \times 10^{-5}$ cubic inches (cu. in.). If one were to deform opening 22 to a more circular shape, the cross-sectional area would be increased and consequently the device would no longer operate as intended, since diluent would be lost from opening 22. For example, if mixing chamber 20 is made to have a circular opening with a diameter of 0.040 inch the double bore catheter will not function properly. Instead it will spill diluent into the blood stream. If, however, opening 22 has a major axis of 0.040 inch with a minor axis of 0.020 inch the long indwelling double bore catheter will work properly.

The length of the catheter can be varied but should ideally be kept within approximately 6 feet to insure adequate response time during continuous measurements of sampled analytes.

Flexible tubing 16 and 17 connect to appropriate instrumentation, such as a suction pump (not shown), for the pumping of a diluent through flexible tubing 16 and bore 18 into mixing chamber 20 and the removal of blood through bore 19 and flexible tubing 17 to analyzing apparatus (not shown), which is situated at a known distance from the catheter and connected thereto via appropriate manifolding. Typically, peristaltic pump tubing is attached to the catheter as part of the fabrication process or may be attached thereafter when the catheter is put into use.

Casing 12 and outerwall 23 can be fabricated from any satisfactory material, including well known organoplastic materials. Flexible tubing 16 and 17 can also be fabricating from any satisfactory material. Typically, the flexible tubing is polyvinyl chloride or polytetrafluoroethylene.

As illustrated, particularly in FIG. 1a, a diluent containing a substance inhibiting coagulation, such as heparin, is introduced through bore 18 into mixing chamber 20 where it mixes (in a manner illustrated at 25) with blood entering through opening 22 and is then returned to analyzing equipment (not shown) through bore 19 and flexible tubing 17. If a pump is used for delivery of diluent, it is adjusted so that its output rate is slightly less than that of the liquid being passed through bore 19 and flexible tube 17. Mixing is limited to mixing chamber 20. Typical flow rates are 0.043 milliliters per minute (ml/min) diluent pumped into the catheter; 0.076 ml/min diluent blood leaving the catheter; and 0.033 ml/min whole blood entering the catheter.

Figure 3:
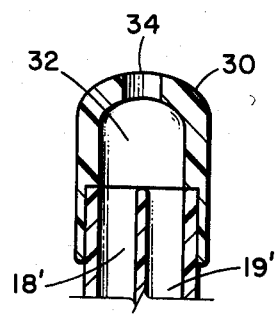
FIGS. 3-5 are partial cross-sectional views of alternative embodiments.

FIG. 3 illustrates an alternative embodiment which comprises a tip 30 which is ultrasonically fused or solvent bonded to double bore 18' and 19' to form mixing chamber 32. Opening 34 is circular in shape and is equal to or less than the combined cross-sectional area of bores 18' and 19'. The distance of mixing chamber 32 from the distal end of bores 18' and 19' to the end of tip 30 is equal to or greater than 2 millimeters and the volume of mixing chamber 32 is between about 3 and about $9 \times 10^{-5}$ cu in.

Figure 4:
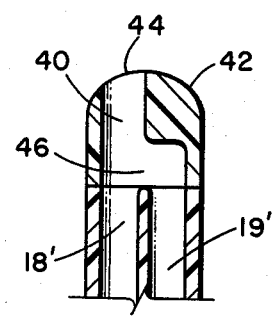

FIG. 4 illustrates still another alternative embodiment in which mixing chamber 40 is formed by attaching tip 42 to the distal end of bores 18' and 19'. Mixing chamber 40 connects with circular opening 44 at one side and bore 18' and passage 46 at the other end. Passage 46 interconnects with bore 19' for the passage of blood to analyzing equipment (not shown). The dimensions of opening 44 and mixing chamber 40 are similar to those for opening 34 and mixing chamber 32 in FIG. 3.

Figure 5:
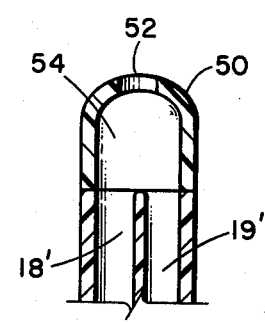

FIG. 5 illustrates still another embodiment comprising a tip 50 fused or bonded in a fluid tight seal to the distal end of bore 18' and 19'. This embodiment has an opening 52 which is circular in configuration and which permits blood to enter mixing chamber 54 where it mixes with the anticoagulant mixture. The dimensions of opening 52 and mixing chamber 54 are substantially identical to those for opening 34 and mixing chamber 32 in FIG. 3.

From the foregoing, it will be seen that this invention is well adapted to attain all of the ends and objects hereinabove set forth, together with other advantages which are obvious and which are inherent to the system. The apparatus of the present invention has the advantages of convenience, simplicity, relative inexpensiveness, dimensional stability, effectiveness, durability, accuracy and directness of action. The invention substantially overcomes the problems associated with the prior art in that it can be used as a long indwelling catheter, it is not position sensitive, it achieves desired mixing of anticoagulant material with blood and it prevents the flow of anticoagulant material into the blood stream. These objectives are achieved while maintaining small, easily manufactured construction features.

While the ideal volume of the mixing chambers is between about 3 and about $9 \times 10^{-5}$ cu. in. it is to be understood that mixing chambers having volumes less than $3 \times 10^{-5}$ cu. in. can be employed as well as mixing chambers having volumes greater than $9 \times 10^{5}$ cu. in. However, if the mixing chanber is less than $3 \times 10^{-5}$ cu. in. there is a risk that incomplete mixing will occur and if the mixing chamber is greater than $9 \times 10^{-5}$ cu. in. the response time may be too long.

Obviously, many other modifications and variations of the invention as hereinbefore set forth may be made without departing from the spirit and scope thereof.

What is claimed is:

1. A long indwelling side-by-side double bore catheter for dilution and sampling of body fluid on a continuing basis for a long period of time, said double bore catheter having flush distal ends of the side-by-side double bores and consisting essentially of:
   a small mixing chamber located at the flush distal ends of said side-by-side double bores, wherein the mixing chamber has a rounded end and a noncircular opening which communicates with the body fluid to be sampled, said opening having a cross-sectional area equal to or less than twice the combined cross-sectional areas of the side-by-side double bores, and wherein the length of the mixing chamber from the flush distal ends of the double bores to the end of the catheter is equal to or greater than 0.07 inch and the volume of said mixing chamber is between about 3 and about 9 times $10^{-5}$ cubic inches.

* * * * *